US007935857B2

(12) United States Patent  
Beech et al.

(10) Patent No.: US 7,935,857 B2
(45) Date of Patent: May 3, 2011

(54) PRODUCT RECOVERY IN GAS-SOLIDS REACTORS

(75) Inventors: James H. Beech, Kingwood, TX (US); Richard E. Walter, Long Valley, NJ (US); Arun K. Sharma, Alexandria, VA (US); Jeffrey S. Smith, Texas City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 814 days.

(21) Appl. No.: 11/707,225

(22) Filed: Feb. 14, 2007

(65) Prior Publication Data

US 2007/0232843 A1     Oct. 4, 2007

Related U.S. Application Data

(60) Provisional application No. 60/788,147, filed on Mar. 31, 2006.

(51) Int. Cl.
*C07C 1/00* (2006.01)
*B01J 8/26* (2006.01)

(52) U.S. Cl. ........ 585/638; 585/639; 585/640; 422/141; 422/142; 422/143; 422/144; 422/145; 422/146; 422/147

(58) Field of Classification Search ............... 585/638, 585/639, 640; 422/141, 144, 142, 143, 145, 422/146, 147
See application file for complete search history.

(56) References Cited

U.S. PATENT DOCUMENTS

| | | | |
|---|---|---|---|
| 4,364,905 A | 12/1982 | Fahrig et al. |
| 4,499,327 A | 2/1985 | Kaiser |
| 4,597,771 A | 7/1986 | Cheng |
| 4,670,993 A | 6/1987 | Dunaway et al. |
| 4,677,242 A | 6/1987 | Kaiser |
| 4,677,243 A | 6/1987 | Kaiser |
| 4,684,375 A | 8/1987 | Morin et al. |
| 4,752,651 A | 6/1988 | Kaiser |
| 4,973,792 A | 11/1990 | Lewis et al. |
| 5,475,182 A | 12/1995 | Janssen |
| 5,714,662 A | 2/1998 | Vora et al. |
| 5,744,680 A | 4/1998 | Mulvaney, III et al. |
| 5,817,906 A | 10/1998 | Marker et al. |
| 5,914,433 A | 6/1999 | Marker |
| 5,962,762 A | 10/1999 | Sun et al. |
| 5,990,369 A | 11/1999 | Barger et al. |
| 6,005,150 A | 12/1999 | Vora |
| 6,023,005 A | 2/2000 | Lattner et al. |
| 6,040,264 A | 3/2000 | Sun et al. |
| 6,121,503 A | 9/2000 | Janssen et al. |
| 6,121,504 A | 9/2000 | Kuechler et al. |
| 6,166,282 A | 12/2000 | Miller |

(Continued)

FOREIGN PATENT DOCUMENTS

GB   2 171 718    9/1986

(Continued)

*Primary Examiner* — Prem C Singh
(74) *Attorney, Agent, or Firm* — Kevin M. Faulkner; David M. Weisberg

(57) ABSTRACT

A gas-solids reaction system is provided for improving product recovery in a multiple reactor reaction system. The solids of the product gas-solids flows from the multiple reactors are separated out in a separation vessel having a baffled transition zone. Additional product vapor is stripped from the solids as the solids pass through the baffled transition zone. The solids are then returned to the multiple reactors.

30 Claims, 8 Drawing Sheets

U.S. PATENT DOCUMENTS

| | | |
|---|---|---|
| 6,187,983 B1 | 2/2001 | Sun |
| 6,303,839 B1 | 10/2001 | Marker |
| 6,303,841 B1 | 10/2001 | Senetar et al. |
| 6,441,261 B1 | 8/2002 | Kuechler et al. |
| 6,455,747 B1 | 9/2002 | Lattner et al. |
| 6,455,749 B1 | 9/2002 | Vaughn |
| 6,482,998 B1 | 11/2002 | Kuechler et al. |
| 6,482,999 B2 | 11/2002 | Fung et al. |
| 2001/0020119 A1 | 9/2001 | Janssen et al. |
| 2002/0087041 A1 | 7/2002 | Kuechler et al. |
| 2003/0004384 A1 | 1/2003 | Coute et al. |
| 2005/0043577 A1 * | 2/2005 | Beech et al. .......... 585/640 |
| 2007/0004949 A1 | 1/2007 | Beech, Jr. et al. |
| 2007/0049782 A1 | 3/2007 | Patel et al. |
| 2007/0227356 A1 | 10/2007 | Beech |

FOREIGN PATENT DOCUMENTS

| | | |
|---|---|---|
| WO | WO 97/36845 | 10/1997 |
| WO | WO 98/02471 | 1/1998 |
| WO | WO 00/41986 | 7/2000 |
| WO | WO 01/62689 | 8/2001 |
| WO | WO 01/94282 | 12/2001 |
| WO | WO 02/32837 | 4/2002 |
| WO | WO 2005/061418 | 7/2005 |

* cited by examiner

Flux values represent flux in standpipes.

PRODUCT RECOVERY IN GAS-SOLIDS REACTORS

CROSS-REFERENCE TO RELATED APPLICATIONS

This application claims priority to application Ser. No. 60/788,147, filed Mar. 31, 2006, which is hereby incorporated by reference.

FIELD OF THE INVENTION

This invention is directed to an apparatus and method for separating gases from solid catalyst particles in a reaction system using a gas-solids flow.

BACKGROUND OF THE INVENTION

Riser reactors provide a convenient reaction system for performing gas-solids reactions. Gas phase reactants can be brought into contact with solid catalyst while inside the riser to convert the reactants into a desired product. Upon exiting the riser, the conversion product is separated from the solids to recover the catalyst.

In reaction systems where only a fraction of the solid catalyst is regenerated during each loop through the system, product vapors generated during one pass through the standpipe or riser reactor can stay with the catalyst during the next pass through the riser reactor. Passing the product vapors through the riser reactor a second time can lead to excess reaction, which can lead to undesirable products and possibly reduce the operating efficiency of the reaction system.

The above problems are further compounded in multiple riser systems. In order to maintain control over the gas-solids reaction, the average state of the solid catalyst in each riser must be the same. To achieve this, a roughly equal amount of regenerated and non-regenerated catalyst must be introduced into each of the multiple risers.

U.S. Pat. No. 4,364,905 describes a single riser FCC reaction system for improving the separation of entrained product vapors from spent catalyst. A stripping gas is flowed through the spent catalyst as it passes through a baffled region. All of the catalyst is then sent to a regenerator.

What is needed is a system and method for improving the separation of gas phase conversion product from catalyst solids. The system and method should be compatible with reaction systems having multiple risers. The system and method should also allow for roughly even distribution of regenerated and non-regenerated catalyst particles into the multiple risers.

SUMMARY OF THE INVENTION

In an embodiment, a method is provided for separating solids from a gas-solids flow. A plurality of product gas-solids flows is produced by performing an oxygenate to olefin conversion reaction in a plurality of reactors. Each of the plurality of product gas-solids flows is separated into a corresponding higher density flow and lower density flow, each higher density flow comprising a majority of the solids contained in the corresponding product gas-solids flow. The solids from each higher density flow are received in a transition zone. Preferably, the transition zone can include one or more layers of baffles. A displacing gas can be countercurrently flowed through the received solids while passing the received solids through the baffled transition zone. Preferably, the displacing gas is flowed from one or more displacing gas inlets within the transition zone. After passing through the transition zone, the received solids are returned to the plurality of reactors via standpipes, the entry locations for each standpipe being separated from the one or more displacing gas inlets by a separation distance.

In another embodiment, an apparatus is provided for performing oxygenate to olefin reactions. The apparatus includes a plurality of oxygenate to olefin reactors. A separation vessel receives the product gas-solids flow from each of the oxygenate to olefin reactors. The separation vessel includes a plurality of separation devices, a transition zone, and one or more displacing gas inlets within the transition zone. Preferably, the transition zone includes one or more layers of baffles. A plurality of standpipe entry locations are separated from the one or more displacing gas inlets by a separation distance. Catalyst entering the standpipe entry locations is returned to the plurality of oxygenate to olefin reactors.

DETAILED DESCRIPTION OF THE INVENTION

Overview

Figure 1:
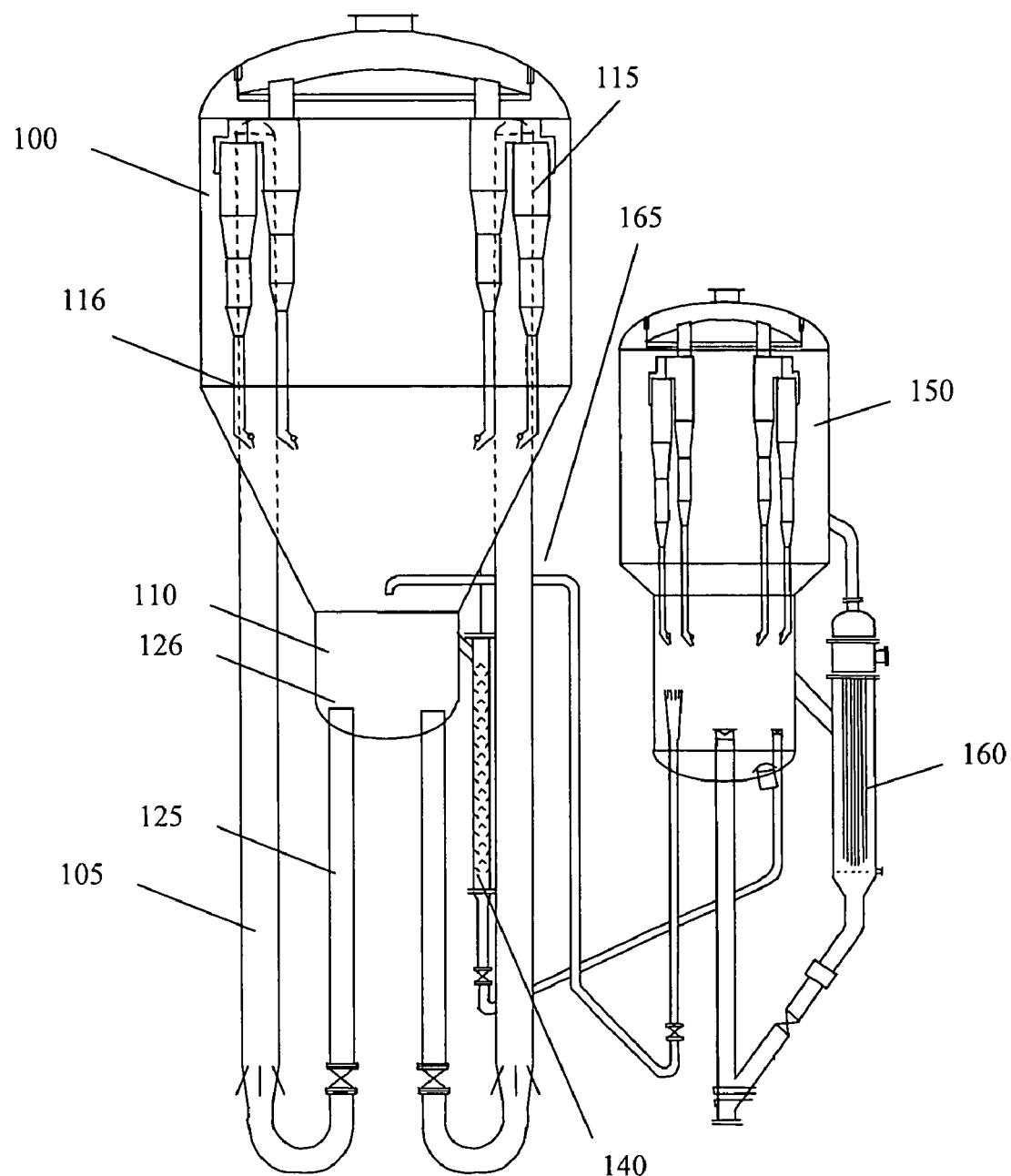
FIG. 1 schematically shows a reaction system according to an embodiment of the invention.

In gas-solids reactions such as oxygenate to olefin reactions, reaction systems having multiple riser reactors connected to a single gas-solids separation vessel can be desirable. For example, a single reaction system with 4 risers allows a roughly fourfold increase in processing capacity without having the same increase in equipment footprint. Using multiple risers, however, raises concerns not present in a single riser reaction system. In particular, the catalyst circulating through each riser in the multiple riser reaction system should have roughly the same catalytic activity. Otherwise, gas-solids flow conditions that provide optimized performance for one riser will not correspond to optimized performance for other risers. An additional concern is the removal of product gas that is entrained with the solid catalyst. Using conventional separation devices, the solids separated out from the gas-solids flow can still include from 2-5% of the desired gas phase product from the reaction.

The 2-5% of gas phase product which is entrained in the solids flow is in an environment with a large amount of catalyst surface area. As the solids flow is routed through the system to return to the riser reactor, the entrained gas phase product can continue to react. The reaction also continues as the entrained gas phase product is passed through the riser for a second time. This extended exposure of gas phase product to the solid catalyst results in additional coke formation and other over-reaction products, such as saturated hydrocarbons.

In addition to not being desirable end products, any coke and/or other over-reaction products formed on the catalyst have the potential to modify the reactivity of the catalyst. This can lead to changes in the expected operation of the gas-solids reaction within the riser. Thus, separating out some or all of this product gas and preventing it from entering the riser will not only increase the amount of product recovered from the reaction system, but it will also reduce the amount of undesired products that could lead to degradation of the system performance.

In various embodiments, this invention provides a system and method for improving the separation of product gases from solid catalyst in a multiple riser and standpipe reaction system. The system and method also allow for roughly equivalent distribution of catalyst to each of the multiple standpipes and therefore risers in gas-solids reactions where only a portion of the solid catalyst is regenerated during each cycle through the reaction system. Preferably, the multiple riser reaction system comprises at least 2 risers, or at least 3 risers, or at least 4 risers, or at least 5 risers.

In an embodiment, improved separation of product gases from solid catalyst can be achieved by passing the catalyst through a transition zone containing a series of baffle structures and one or more gas delivery inlets, such as one or more gas spargers. Catalyst from the regenerator is also returned to the top of the transition zone, to allow time for the regenerated and non-regenerated catalyst to mix and/or distribute evenly. At the bottom of the transition zone, the catalyst passes into the standpipe entry for each riser. To facilitate the flow of catalyst through the reaction system, the bottom of the baffle region is separated from the standpipe entry locations by a minimum distance.

In various embodiments, the structures in the transition zone facilitate improved separation of product gases from the solid catalyst. As the solid catalyst travels down through the baffles, the solid catalyst is contacted with a gas introduced via the gas delivery inlets. In an embodiment, these inlets can be positioned just below the last tier of baffles. The gas introduced by the gas inlets can be steam, nitrogen, or another gas that will not react in the separation vessel with the solid catalyst or the product.

Figure 3:
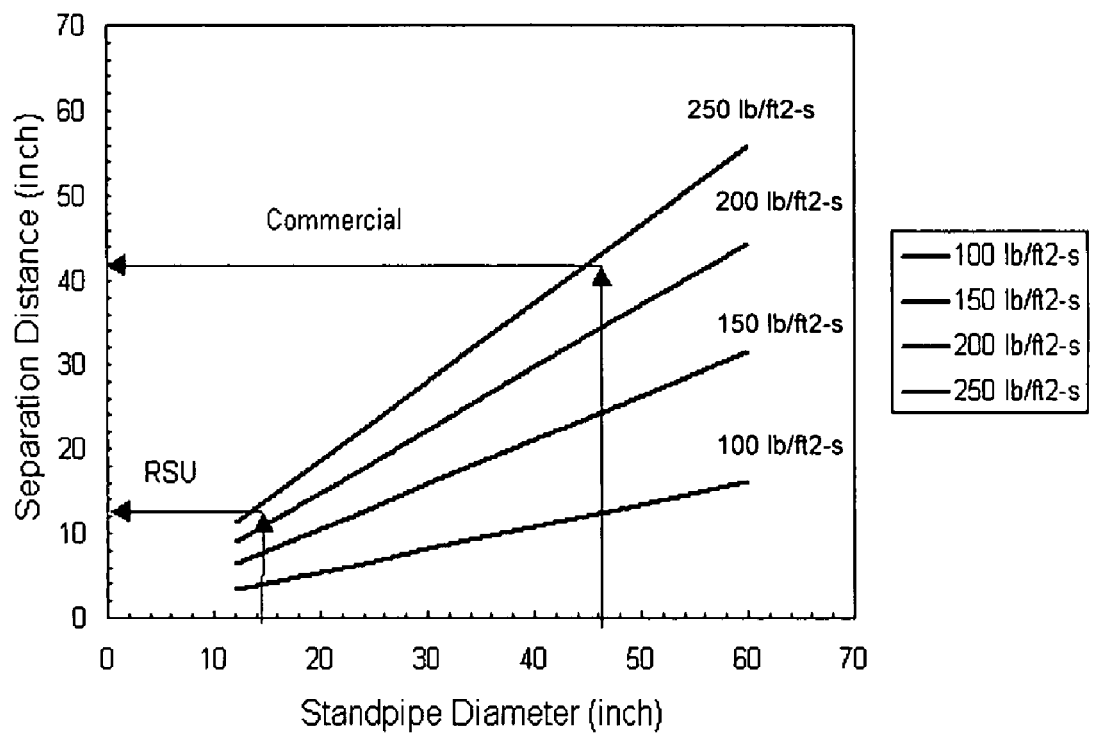
FIG. 3 shows expected performance characteristics for an apparatus according to an embodiment of the invention.

To facilitate the flow of solid catalyst through the reaction system, the bottom row of baffles and/or the gas delivery inlets are separated from the riser feed standpipe entrances by a minimum distance. The separation distance is dependent on the diameter of the standpipes at the entry location and the desired solid catalyst flux through the standpipes and reaction system. Larger distances between the riser standpipe entry and the gas delivery inlets and/or bottom row of baffles will allow for higher catalyst flux through the standpipes and reaction system, for a given standpipe diameter, while larger diameters for the standpipes will reduce the maximum stable catalyst flux, for a given separation distance as shown in FIG. 3. This effect is caused by the amount of de-aeration taking place, with a longer separation distance providing more de-aeration and allowing higher flux. However, too much de-aeration, such as due to having too long of a separation distance, can lead to a risk of complete defluidization and a sudden loss of catalyst flow.

Flow of Solid Catalyst in a Multiple Riser Reaction System

In various embodiments, riser reactors can be used to perform a variety of gas-solids reactions. Generally, solid particles for catalyzing a reaction are introduced into the riser. A reactive feedstock is then flowed into the riser. As the feedstock reacts and flows up through the riser, solid particles become entrained in the feedstock flow. The solid particles are then preferably removed from the gas-solids flow after exiting the riser. In an embodiment, the riser can have a diameter of at least 1 meter, or at least 1.5 meters, or at least 2 meters, or at least 3 meters, or at least 4 meters, or at least 5 meters, or at least 6 meters. In another embodiment, the riser can have a diameter of 9 meters or less, or 8 meters or less, or 7 meters or less, or 6 meters or less, or 5 meters or less, or 4 meters or less. Note that the diameter of the riser can vary over the length of the riser. For the purposes of this invention, the diameter of the riser refers to the diameter of the riser at the location where the riser is joined to a termination device.

After the gas-solids flow leaves the riser, the solid particles are removed from the gas-solids flow by passing the mixture of gas and solids through one or more separation devices, such as cyclone separators. To increase the efficiency of removal, the gas-solids flow can be passed through multiple stages of separators.

In an embodiment, a gas-solids flow can be transferred from a riser to a separation device by coupling the riser to one or more separators. The riser and separators can be coupled in any convenient manner. For example, the riser can be closely coupled to a separator by providing one or more closed conduits between the riser and one or more separators. In a preferred embodiment, the closed conduits are substantially sealed to prevent losses from the gas-solids flow to the surrounding environment prior to entering the first separator, with only a small vent gap placed between the riser termination device and the first separation device or placed between the first and second separation devices to allow separation vessel vapors to escape.

As the gas-solids flow passes through the separation devices, the flow is separated into a higher density (primarily solids) flow and lower density (primarily gas) flow by each device. For example, in an embodiment where the separation devices are cyclone separator stages, each stage produces a higher density flow that exits the cyclone separator stage through a dipleg. The lower density flow is either passed into the next cyclone separator stage, or after the final stage the lower density flow is passed out of the separation vessel. Because the cyclone separator stages are not perfectly efficient, some product gas will be entrained with the higher density flow as it exits through the dipleg.

After exiting the dipleg, the solid catalyst from a higher density flow (and any entrained product vapor) is received into a transition zone in the separation vessel. The transition zone includes a fluidized bed of the catalyst solids. The solid catalyst bed is the source of solid catalyst for feeding the risers or standpipes to continue the gas-solids reaction. Preferably, a portion of the solid catalyst from the catalyst bed and/or the higher density flows exiting the cyclone separator stages can be diverted into a regenerator. The location in the transition zone for withdrawing catalyst for diversion to the regenerator can be at any convenient height of the catalyst bed held within the transition zone. When catalyst is returned from the regenerator, the catalyst can be distributed at the top of the catalyst bed. The distribution method for returning the catalyst to the top of the catalyst bed can be any conventional catalyst distribution method.

The standpipes and/or standpipe entries can also have a range of diameters. In various embodiments, the standpipes can have a constant diameter throughout, or the diameter of the standpipes can vary along the standpipe. In an embodiment, the standpipe entry can have a diameter of at least 0.5 meters, or at least 0.75 meters, or at least 1 meter. In another embodiment, the standpipe entry can have a diameter of 2 meters or less, or 1.75 meters or less, or 1.5 meters or less. The diameter of the standpipe entry is measured at the location where the solid catalyst enters the standpipe.

FIG. 1 schematically shows an embodiment of a reaction system suitable for performing the invention. In the embodiment shown in FIG. 1, a plurality of riser reactors 105 are provided for performing a gas-solids reaction. The tops of risers 105 are not shown as they are contained within separation vessel 100. The exits near the top of each riser are coupled with cyclone separator stages 115. During operation, solids separated out by the cyclone separator stages 115 passes out of the diplegs 116 and toward transition zone 110 of separation vessel 100. Preferably, a catalyst bed will be formed by the catalyst in the bottom region. This catalyst bed feeds catalyst to the standpipe entry locations 126 for the standpipes 125. A portion of the catalyst in the catalyst bed can be diverted to regenerator 150 via the conduit containing catalyst stripper 140. Regenerator 150 is optionally provided with a catalyst cooler 160. Regenerated catalyst can be returned via conduit 165. In the embodiment shown in FIG. 1, regenerated catalyst is returned to the top of the transition zone to join the catalyst exiting the cyclone diplegs. More generally, regenerated catalyst can be distributed at the top of the catalyst bed in the transition zone by any conventional catalyst distribution device known in the art.

Transition Zone Structure

In an embodiment, the transition zone includes a plurality of baffles that solid catalyst passes around as it moves down through the transition zone. A variety of structures can be used as baffles. For example, the baffles can be a series of bars or other solid structures arranged parallel to each other that span the interior of the transition zone at a given height in the transition zone. In other embodiments, the baffles can be sheds, gratings, packing, or any other suitable solid structures. In an embodiment, multiple levels of baffles can be used. In such an embodiment, the baffles can resemble a series of sheds, gratings, or other solid structures placed in the transition zone for the solid catalyst to pass through. The solid structure portions in each level can be aligned, or the solid structure portions can be offset so that the openings in one level of baffles align with the solid structure portions of the subsequent level. Other arrangements, such as aligning the solid structure portions of baffle levels perpendicular to each other, or rotating the baffles at another angle, can also be selected. In an embodiment, at least 2 levels of baffle structures can be used, or at least 4, or at least 5, or at least 6, or at least 8. In another embodiment, 10 or less levels of baffle structures can be used, or 8 or less, or 6 or less. In still another embodiment, baffles can be arranged in pairs of levels. Within a pair of baffle levels, the baffles in one level can be matched with the baffles in the second level. For example, the baffles in one level can be rotated 90 degrees relative to the second level. Alternatively, the baffles in one level can be offset to align openings in one level with solid portions in the second level.

In an embodiment, the solid structures used to form the baffles can have various geometries. For example, the solid structures can have a rectangular profile, a triangular profile, or any other convenient solid geometry. In another embodiment, the baffles can be in the form of "sheds." The sheds can have a "v-shaped" profile that is inverted so that the catalyst approaches the point of the "v" as the catalyst moves through the transition zone. Preferably, the sheds can also include a small vertical surface at the bottom edges of the inverted v-shape. Various orientations can be selected for the sheds. All of the sheds can be aligned, or each successive level of sheds can be oriented at an offset, such as a 90 degree offset. Similarly, the positioning of the sheds in each level can offset, as noted above. In still another embodiment, a commercially available packing material such as Koch Glitsch FCC stripper packing can be used as a baffle material.

In an embodiment, the baffles can be perforated, or otherwise have openings to allow gas to pass through the baffle structure. For example, the baffles can have a series of 1 cm to 3 cm diameter holes spaced evenly along the length of the baffle, or in more than one row spread evenly along the length of the baffle. The holes can be separated by at least 2 cm, or at least 3 cm, or at least 4 cm. Alternatively, the holes can be 6 cm or less apart, or 5 cm or less apart, or 4 cm or less apart.

In still another embodiment, one or more gas spargers or other gas inlets can be provided in the transition zone. Preferably, the gas inlets can be located below the lowest level of baffles within the transition zone. Alternatively, the gas inlet structures can serve as the lowest level of baffles within the transition zone.

The flow rate of steam, nitrogen, or other gas out of the gas spargers can be characterized in terms of a superficial velocity. The superficial velocity of the gas emerging from the gas spargers can be determined by taking the total flow rate of gas and dividing it by the cross sectional area of the separation vessel in the transition zone. Dimensionally, this corresponds to a flow rate for the gas in the direction perpendicular to the cross-section of the transition zone. Preferably, the superficial velocity of the gas introduced by the gas spargers is 0.03 m/sec or greater, or 0.10 m/sec or greater, or 0.15 m/sec or greater. In another embodiment, the superficial velocity of the gas introduced by the gas spargers is 0.30 m/sec or less, or 0.25 m/sec or less, or 0.20 m/sec or less.

Figure 2A:
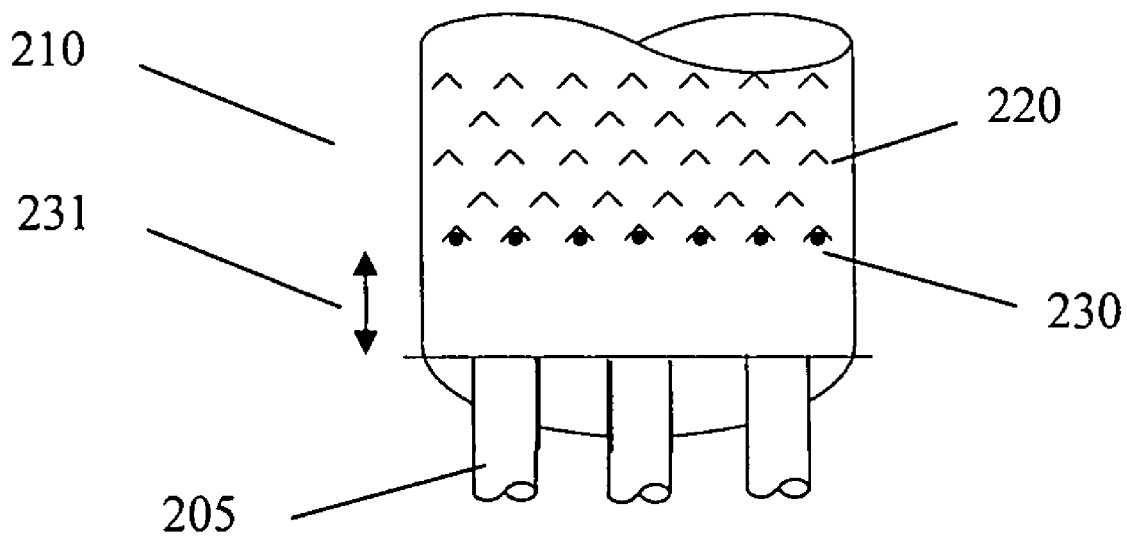
FIGS. 2A and 2B schematically show a portion of a reaction system according to an embodiment of the invention.
Figure 2B:
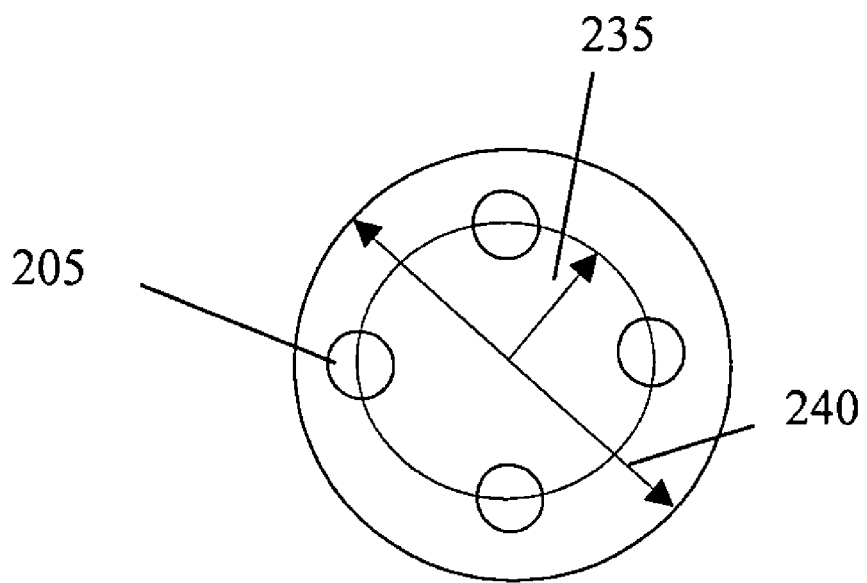

FIGS. 2A and 2B schematically shows an example of a transition zone 210 in a separation vessel according to an embodiment of the invention. FIG. 2A shows a side view of the transition zone 210. In the embodiment shown in FIG. 2A, 5 levels of baffles 220 are used. Each level of baffles is oriented perpendicular to the plane of the drawing. The baffle structures in successive levels are offset from one another, so that an open space in one level is positioned above a baffle structure in the next level. In the embodiment depicted, the baffle structures are inverted v-shaped structures. Preferably, a vertical piece can be attached to the bottom edge of each v-shaped structure. A series of gas spargers 230 is also located underneath the lowest level of baffle structures 220. Preferably, each of the baffle structures 220 is perforated to allow gas to pass through the structures. The gas spargers 230 are separated from the entry locations for the standpipes 205 by a distance 231.

Figure 4:
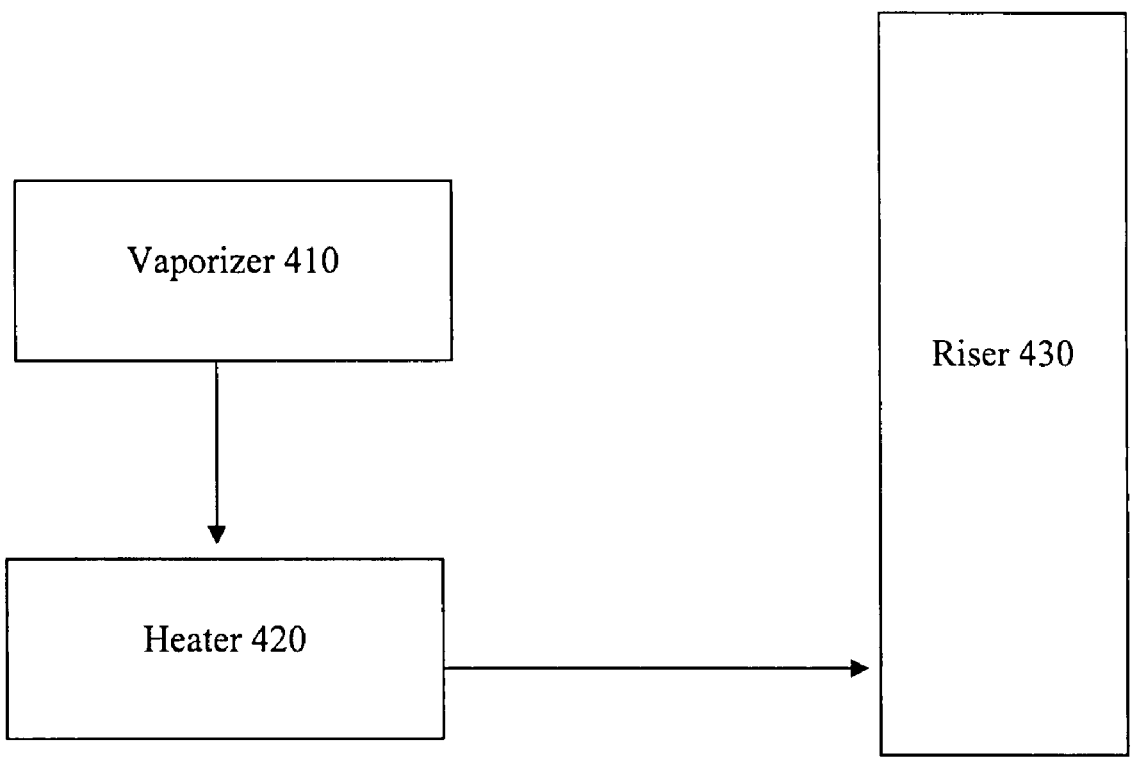
FIG. 4 schematically shows another portion of an apparatus according to an embodiment of the invention.

FIG. 2B depicts a top-down cross-sectional view of the transition zone. As shown in FIG. 2B, 4 standpipes 205 are connected to the separation vessel that includes transition zone 210. FIG. 2B also shows a comparison between a radius 235 from the center of the transition zone 210 to the center of the standpipes 205, and the overall diameter 240 of the transition zone. In this example, the ratio of the radius to the center of the standpipes and the diameter of the transition zone is 0.32. In other embodiments, this ratio can be at least 0.2, or at least 0.25, or at least 0.3. In still other embodiments, this ratio can be 0.4 or less, or 0.35 or less.

FIG. 3 depicts the expected maximum stable standpipe catalyst flux characteristics for various gas-solids flows in a reaction system according to an embodiment of the invention. These expected flow characteristics are based on a multiple riser reaction system with a single separation vessel. The transition zone of the separation vessel is similar to the transition zone shown in FIGS. 2A and 2B. The data shown in FIG. 3 corresponds to a maximum stable flux for solids in the gas solids flow. As shown in FIG. 3, the maximum stable flux increases as the distance (height) increases between the gas inlets (spargers) and the standpipe entry locations. The lowest catalyst flux shown is 100 lb/ft$^2$*sec (488 kg/m$^2$*sec), which corresponds to a typical minimum desired catalyst flux within the standpipe. At a typical commercial standpipe diameter of 46 inches (117 cm), a separation of roughly 10 inches (25 cm) would be required between the bottom of the gas spargers and the entry point for the catalyst into the standpipes. At the same standpipe diameter, maintaining a desirable commercial value of 250 lb/ft$^2$*sec (1221 kg/m$^2$*sec) requires a separation distance of about 40 inches (102 cm) between the gas spargers and the standpipes. Note that too large of a separation distance at a given standpipe diameter can result in complete catalyst de-fluidization at the standpipe entry and loss of catalyst flow.

More generally, in various embodiments, the distance between the gas spargers (or other gas inlets) and the entry locations for the standpipes can be at least 10 inches (25 cm), or at least 50 cm, or at least 75 cm, or at least 100 cm. In other embodiments, the distance between the gas spargers (or other gas inlets) and the entry locations for the standpipes can be 300 cm or less, or 250 cm or less, or 200 cm or less.

An alternative way of determining suitable values for catalyst flux is by considering the properties of the catalyst bed in the transition zone. One possible metric is the rate of change (or gradient) in the density of the catalyst between the gas spargers and the entry locations for the standpipes. Preferably, the absolute density within the transition zone can be between 50%-90% of the catalyst minimum fluidization density. In an embodiment, the density of fluidized material within the transition zone can be at least 25 lb/ft$^3$, or at least 30 lb/ft$^3$. In another embodiment, the density of the fluidized material in the transition zone can be 45 lb/ft$^3$ or less, or 40 lb/ft$^3$ or less. It is believed that a density gradient greater than about 5 lb/ft$^3$*ft (266 kg/m$^3$*m) will result in reduced value for the maximum catalyst flux that can flow through a reaction system. Thus, in various embodiments the reaction system can be operated to have a density gradient of 10 lb/ft$^3$-ft (525 kg/m$^3$-m) or less, or 5 lb/ft$^3$-ft (263 kg/m$^3$-m) or less, or 4 lb/ft$^3$-ft (210 kg/m$^3$-m) or less, or 3 lb/ft$^3$-ft (158 kg/m$^3$-m) or less, or 1 b/ft$^3$-ft (53 kg/m$^3$-m) or less.

The catalyst flux within the transition zone can also be characterized. In an embodiment, the catalyst flux within the transition zone can be 100 lb/ft$^2$*sec (488 kg/m$^2$*sec) or less, or 50 lb/ft$^2$*sec (244 kg/m$^2$*sec) or less, or 35 lb/ft$^2$*sec (170 kg/M$^2$*sec) or less, or 20 lb/ft$^2$*sec (98 kg/M$^2$*sec) or less. In another embodiment, the catalyst flux within the transition zone can be at least 1 lb/ft$^2$*sec (5 kg/m$^2$*sec), or at least 5 lb/ft$^2$*sec (24 kg/m$^2$*sec), or at least 10 lb/ft$^2$*sec (49 kg/m$^2$*sec).

Another metric that can be used is the residence time of catalyst within the transition zone. In an embodiment, the residence time for catalyst in the transition zone can be 60 minutes or less, or 10 minutes or less, or 1 minute or less. In another embodiment, the residence time can be at least 5 seconds, or at least 10 seconds, or at least 30 seconds.

Still another metric is the amount of "defluidization" of the solid catalyst. As solid catalyst flows below the gas inlet (such as a gas sparger), the total amount of gas in contact with the solid catalyst will be gradually reduced. If the quantity of gas is too low, the solid catalyst could lose some or all of its fluidization properties. This would result in poor flow behavior for the catalyst in the bed below the gas inlet. To avoid this, the distance between the gas spargers and the entry locations to the standpipes should be close enough so that the solid catalyst retains a desired level of fluidization. In order to quantify the level of fluidization of a catalyst bed, the "defluidization" of the catalyst can be expressed as the volume fraction of gas bubbles in the catalyst relative to the total volume of the gas/catalyst mixture. In an embodiment, the defluidization of the solid catalyst at the entry location for the standpipes can be 0.00005 or more, or 0.0001 or more, or 0.0002 or more.

Oxygenate to Olefin Reactions

An example of a reaction system that benefits from this invention is an oxygenate-to-olefin process, such as a methanol to olefin conversion reaction. Conventionally, oxygenate-to-olefin processes are carried out in a fluidized bed, fast fluidized bed, or riser reactor configuration where a fluid (gas) flow of a feedstock is passed through a bed of solid catalyst particles. More generally, the processes of this invention are applicable to gas-solids reaction systems where the solids are separated from the gas flow at some point during the reaction process, including systems where the gas is inert. The examples below describe an oxygenate to olefin reaction system that can be improved using the separation process of the invention.

Oxygenates used in this invention include one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to about 80 mole percent, more preferably from about 5 to about 50, most preferably from about 5 to about 25. In another embodiment, other hydrocarbons are added to a feedstock either directly or indirectly, and include olefin(s), paraffin(s), aromatic(s) (see, for example, U.S. Pat. No. 4,677,242, addition of aromatics) or mixtures thereof, preferably propylene, butylene, pentylene, and other hydrocarbons having 4 or more carbon atoms, or mixtures thereof.

In a conventional oxygenate to olefin reaction, a feed containing an oxygenate is contacted in a reaction zone of a reactor apparatus with a molecular sieve catalyst at process conditions effective to produce light olefins, i.e., an effective temperature, pressure, WHSV (weight hour space velocity) and, optionally, an effective amount of diluent, correlated to produce light olefins. Usually, the oxygenate feed is contacted with the catalyst when the oxygenate is in a vapor phase. Alternatively, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions. As used herein, the term reactor includes not only commercial scale reactors but also pilot sized reactor units and lab bench scale reactor units.

The conversion of oxygenates to produce light olefins may be carried out in a variety of large scale catalytic reactors, including, but not limited to, fluid bed reactors and concurrent riser reactors as described in Fluidization Engineering, D. Kunii and O. Levenspiel, Robert E. Krieger Publishing Co. NY, 1977. Additionally, countercurrent free fall reactors may be used in the conversion process. See, for example, U.S. Pat. No. 4,068,136 and Fluidization and Fluid-Particle Systems, pp. 48-59, F. A. Zenz and D. F. Otluner, Reinhold Publishing Corp., NY, 1960.

In one embodiment of this invention, the gas and solid particles are flowed through the gas-solids reactor system at a weight hourly space velocity (WHSV) of from about 1 $hr^{-1}$ to about 5,000 $hr^{-1}$, preferably from about 5 $hr^{-1}$ to about 3,000 $hr^{-1}$, more preferably from about 10 $hr^{-1}$ to about 1,500 $hr^{-1}$, and most preferably from about 20 $hr^{-1}$ to about 1,000 $hr^{-1}$. In one preferred embodiment, the WHSV is greater than 25 $hr^{-1}$, and up to about 500 $hr^{-1}$. In this invention, WHSV is defined as the total weight per hour of the gas flowing between reactor walls divided by the total weight of the solids flowing between the same segment of reactor walls. The WHSV is maintained at a level sufficient to keep the catalyst composition in a fluidized state within a reactor.

In another embodiment of the invention directed toward use of cyclones in conjunction with a riser reactor, the gas and solid particles are flowed through the gas-solids reactor system at a gas superficial velocity (GSV) at least 1 meter per second (m/sec), preferably greater than 2 m/sec, more preferably greater than 3 m/sec, and most preferably greater than 4 m/sec. The GSV should be sufficient to maintaining the solids in a fluidized state, particularly in a fast fluidized state.

In still another embodiment, cyclones configured according to this invention can be used with a fixed fluidized bed reactor. In such an embodiment, the GSV can be as low as 0.03 m/s.

In yet another embodiment of the invention, the solids particles and gas are flowed through the gas-solids reactor at a solids loading of at least 0.1 lb/ft³ (1.6 kg/m³), or at least 0.5 lb/ft³ (8 kg/m³), or at least 1.0 lb/ft³ (16 kg/m³), or at least 2.0 lb/ft³ (32 kg/m³), or at least 4.0 lb/ft³ (64 kg/m³). Alternatively, the solids loading can be 5 lb/ft³ (80 kg/m³) or less, or 4.0 lb/ft³ (64 kg/m³) or less, or 2.0 lb/ft³ (32 kg/m³) or less.

In one practical embodiment, the process is conducted as a fluidized bed process or high velocity fluidized bed process utilizing a reactor system, a regeneration system and a recovery system. In such a process the reactor system conveniently includes a fluid bed reactor system having a first reaction region consisting of various fast fluid or dense fluid beds in series or parallel and a second reaction region within at least one disengaging vessel, comprising two or more cyclones configured and/or operated according to various embodiments of the invention. In one embodiment, the fast fluid or dense fluid beds and disengaging vessel are contained within a single reactor vessel. Fresh feedstock, preferably containing one or more oxygenates, optionally with one or more diluent (s), is fed to the one or more fast fluid or dense fluid beds reactor(s) into which a molecular sieve catalyst composition or coked version thereof is introduced. In one embodiment, prior to being introduced to the reactor(s), the molecular sieve catalyst composition or coked version thereof is contacted with a liquid and/or vapor, preferably water and methanol, and a gas, for example, an inert gas such as nitrogen.

In an embodiment, the amount of fresh feedstock fed as a liquid and/or a vapor to the reactor system is in the range of from 0.1 weight percent to about 99.9 weight percent, such as from about 1 weight percent to about 99 weight percent, more typically from about 5 weight percent to about 95 weight percent based on the total weight of the feedstock including any diluent contained therein. The liquid and vapor feedstocks may be the same composition, or may contain varying proportions of the same or different feedstocks with the same or different diluents.

The process of this invention can be conducted over a wide range of temperatures, such as in the range of from about 200° C. to about 1000° C., for example, from about 250° C. to about 800° C., including from about 250° C. to about 750° C., conveniently from about 300° C. to about 650° C., typically from about 350° C. to about 600° C. and particularly from about 350° C. to about 550° C.

Similarly, the process of this invention can be conducted over a wide range of pressures including autogenous pressure. Typically the partial pressure of the feedstock exclusive of any diluent therein employed in the process is in the range of from about 0.1 kPa to about 5 MPa, such as from about 5 kPa to about 1 MPa, and conveniently from about 20 kPa to about 500 kPa.

In another embodiment of the invention, the ratio of ethylene to propylene in an oxygenate-to-olefin reaction can be controlled by controlling the temperature of the incoming oxygenate feed. The ratio of ethylene to propylene produced in an oxygenate to olefin reaction can be referred to as the Prime Olefin Ratio (POR).

One of the factors that determines the POR is the temperature at the top of the riser in an oxygenate to olefin reaction system. Higher temperatures at the top of the riser will increase the amount of ethylene produced, potentially allowing POR values of 1.2 or greater if the temperature is increased to above 950° F.

One method for increasing the temperature of the oxygenate feedstock vapor is to create a high pressure, saturated vapor feed. A saturated vapor feed can be formed at a high pressure such as 325 psia (2.24 MPa). While this is effective for raising the temperature of the feedstock vapor, the pressure of the vapor has to be reduced prior to introduction into the riser. This leads to cooling of the vapor, which limits the ability to achieve further increases in temperature. As a result, achieving pressures greater than 2.24 MPa does not lead to further increases in feedstock and/or riser top temperatures.

According to embodiments of the invention, an alternate way for increasing the feedstock vapor temperature is to directly heat the vapor at a lower pressure. In such an embodiment, after forming a saturated oxygenate vapor, the vapor can be superheated to a temperature such as at least 300° F. (149° C.), or at least 325° F. (163° C.), or at least 350° F. (177° C.). Heating of the vapor will lead to a small rise in pressure, so the pressure of the vapor is reduced to match the riser pressure prior to introduction. However, the amount of cooling is much less than in the pressurized vapor example above, so higher riser top temperatures can be achieved. In an embodiment, superheating of the oxygenate feedstock can be used to achieve a top riser temperature of at least 975° F. (524° C.), or at least 1000° F. (538° C.), or at least 1025° F. (552° C.), or at least 1050° F. (566° C.).

FIG. 4 schematically shows a portion of an oxygenate to olefin reaction system according to an embodiment of the invention. In the embodiment shown in FIG. 4, methanol vaporizer 410 is used to vaporize methanol (or another oxygenate) for use as feedstock in a conversion reaction. The vaporized methanol is then passed to a heating unit 420 to superheat the vapor. The pressure of the superheated vapor is then reduced to the pressure level of riser 430 for introduction as feedstock.

Figure 5:
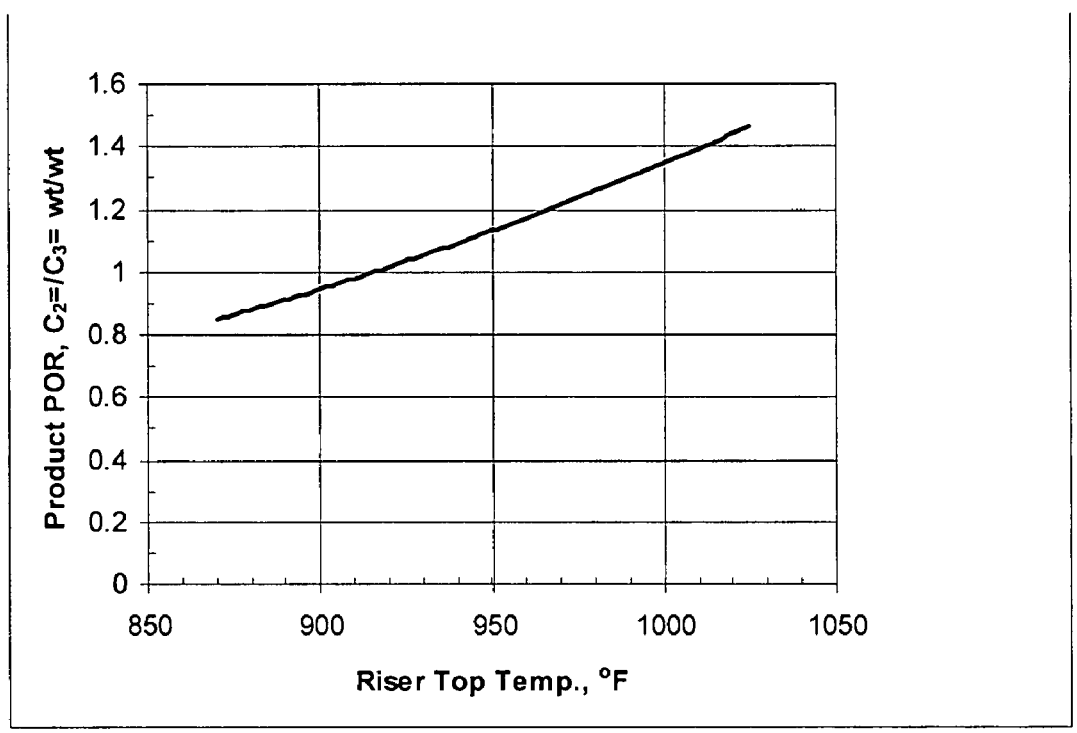
FIG. 5 shows results of operation of an apparatus according to an embodiment of the invention.

FIG. 5 depicts data showing the change in POR as a function of the temperature at the top of the riser. As shown in FIG. 5, increasing the temperature at the top of the riser leads to increasing values of POR, corresponding to increasingly higher proportions of ethylene in the product vapor as compared to propylene.

In embodiments involving a riser reactor, the solids particles and gas are flowed through the gas-solids reactor at a solids to gas mass ratio of about 0.5:1 to about 75:1. Preferably, the solids particles and gas are flowed through the gas-solids reactor at a solids to gas mass ratio of about 8:1 to about 50:1, more preferably from about 10:1 to about 40:1.

During the conversion of a hydrocarbon feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example, greater than 75 weight percent, and preferably greater than 78 weight percent. Typically, the amount ethylene produced in weight percent based on the total weight of hydrocarbon product produced, is greater than 30 weight percent, such as greater than 35 weight percent, for example, greater than 40 weight percent. In addition, the amount of propylene produced in weight percent based on the total weight of hydrocarbon product produced is greater than 20 weight percent, such as greater than 25 weight percent, for example, greater than 30 weight percent, and preferably greater than 35 weight percent.

The feedstock entering the reactor system is preferably converted, partially or fully, in a reaction region into a gaseous effluent. In an embodiment, the reaction region is closely coupled to a plurality of separation devices, such as cyclone separators. In another embodiment, the gaseous effluent enters a disengaging vessel along with the coked catalyst composition. In such an embodiment, the disengaging vessel includes cyclone separators configured and/or operated according to the invention. In still another embodiment, the disengaging vessel also includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition. After exiting the separation devices and/or disengaging vessels, some or all of the catalyst can then be introduced to a regeneration system.

In an embodiment, at least a portion of the coked catalyst composition is withdrawn from one or more of the disengaging vessels and introduced to the regeneration system. The regeneration system comprises a regenerator where the coked catalyst composition is contacted with a regeneration medium, preferably a gas containing oxygen, under conventional regeneration conditions of temperature, pressure and residence time. In an embodiment, a gas-solids flow exiting a regenerator may be passed through cyclones configured according to the invention. Alternatively, at least a portion of the catalyst can be flowed to bypass the regeneration system. The catalyst bypassing the regenerator can be flowed to another desired portion of the reaction system, such as flowing the catalyst directly into a catalyst cooler or allowing the catalyst to rejoin a fluidized bed in the reactor. Preferably, the catalyst bypassing the regenerator is approximately evenly distributed into each of a plurality of standpipe entry locations.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example, from about 450° C. to about 750° C., and conveniently from about 550° C. to about 700° C. The regeneration pressure may be in the range of from about 15 psia (103 kPa) to about 500 psia (3448 kPa), such as from about 20 psia (138 kPa) to about 250 psia (1724 kPa), including from about 25 psia (172 kPa) to about 150 psia (1034 kPa), and conveniently from about 30 psia (207 kPa) to about 60 psia (414 kPa).

The residence time of the catalyst composition in the regenerator may be in the range of from about one minute to several hours, such as from about one minute to 100 minutes. The amount of oxygen in the regeneration flue gas (i.e., gas which leaves the regenerator) may be in the range of from about 0.01 mole percent to about 5 mole percent based on the total volume of the gas. The amount of oxygen in the gas used to regenerate the coked catalyst (i.e., fresh or feed gas) is typically at least about 15 mole percent, preferably at least about 20 mole percent, and more preferably from about 20 mole percent to about 30 mole percent, based on total amount of regeneration gas fed to the regenerator.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture).

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the reactor(s). In a preferred embodiment, the regenerated catalyst is returned to the transition zone in the separation vessel. This allows the regenerated catalyst to be combined with the non-regenerated catalyst for even distribution between each of the multiple standpipe entry locations. In another embodiment, the regenerated catalyst composition withdrawn from the regeneration system is returned to the reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, Experimental Techniques, Circulating Fluidized Beds, Grace, Avidan and Knowlton, eds., Blackie, pp. 336-337, 1997.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example, from about 0.2 weight percent to about 5 weight percent, and conveniently from about 0.3 weight percent to about 2 weight percent based on the weight of the molecular sieve.

The gaseous reactor effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture and other derivative processes such as aldehydes, ketones and ester manufacture, and other associated equipment, for example, various condensers, heat exchangers, refrigeration systems or chill trains, compressors, knockout drums or pots, pumps, and the like.

Non-limiting examples of these towers, columns, splitters or trains used alone or in combination include one or more of a demethanizer, preferably a high temperature demethanizer, a deethanizer, a depropanizer, a wash tower often referred to as a caustic wash tower and/or quench tower, absorbers, adsorbers, membranes, ethylene (C2) splitter, propylene (C3) splitter and butene (C4) splitter.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Typically, in converting one or more oxygenates to olefin (s) having 2 or 3 carbon atoms, a minor amount of hydrocarbons, particularly olefin(s), having 4 or more carbon atoms is also produced. The amount of $C_4+$ hydrocarbons is normally less than 20 weight percent, such as less than 10 weight percent, for example, less than 5 weight percent, and particularly less than 2 weight percent, based on the total weight of the effluent gas withdrawn from the process, excluding water. Typically, therefore the recovery system may include one or more reaction systems for converting the $C_4+$ impurities to useful products.

Additional Types of Reaction Systems

The techniques of this invention are potentially useful in any multiple riser reaction system for performing reactions involving solid particles entrained in a gas-solids flow. Non-limiting examples of such reaction systems include reaction systems selected from the group consisting of catalytic cracking reaction systems, transalkylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing aromatics, systems for converting oxygenates (e.g., alcohols) to olefins, systems for converting oxygenates (e.g., alcohols) to aromatics or gasoline, systems for oligomerizing olefins, and systems for converting unsaturated hydrocarbons to aldehydes. More specifically, such examples include:

A) The catalytic cracking of a naphtha feed to produce light olefins. Typical reaction conditions include from about 500° C. to about 750° C., pressures of subatmospheric or atmospheric, generally ranging up to about 10 atmospheres (gauge; 1013 kPa) and residence time (time of contact of feed and/or product with catalyst) from about 10 milliseconds to about 10 seconds;

B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (10 kPa) to about 30 atmospheres (3040 kPa), and weight hourly space velocities of from about $0.1\ hr^{-1}$ to about $100\ hr^{-1}$;

C) The transalkylation of aromatic hydrocarbons in the presence of polyalkylaromatic hydrocarbons. Typical reaction conditions include a temperature of from about 200° C. to about 500° C., a pressure of from about one atmosphere (101 kPa) to about 200 atmospheres (20.3 MPa), a weight hourly space velocity of from about $1\ hr^{-1}$ to about $100\ hr^{-1}$, and an aromatic hydrocarbon/polyalkylaromatic hydrocarbon mole ratio of from about 1/1 to about 16/1;

D) The isomerization of aromatic (e.g., xylene) feedstock components. Typical reaction conditions for such include a temperature of from about 230° C. to about 510° C., a pressure of from about 0.5 atmospheres (51 kPa) to about 50 atmospheres (5.1 MPa), a weight hourly space velocity of from about $0.1\ hr^{-1}$ to about $200\ hr^{-1}$, and a hydrogen/hydrocarbon mole ratio of from about 0 to about 100/1;

E) The catalytic dewaxing of hydrocarbons by selectively removing straight chain paraffins. The reaction conditions are dependent in large measure on the feed used and upon the desired pour point. Typical reaction conditions include a temperature between about 200° C. and 450° C., a pressure of up to 3,000 psig and a liquid hourly space velocity from $0.1\ hr^{-1}$ to $20\ hr^{-1}$;

F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about one atmosphere (101 kPa) to about 200 atmospheres (20.3 MPa), a weight hourly space velocity of from about 1 hr$^{-1}$ to about 100 hr$^{-1}$, and an aromatic hydrocarbon/alkylating agent mole ratio of from about 1/1 to about 20/1;

G) The alkylation of aromatic hydrocarbons, e.g., benzene, with long chain olefins, e.g., $C_{14}$ olefin. Typical reaction conditions include a temperature of from about 50° C. to about 200° C., a pressure of from about one atmosphere (101 kPa) to about 200 atmospheres (20.3 MPa), a weight hourly space velocity of from about 2 hr$^{-1}$ to about 2000 hr$^{-1}$, and an aromatic hydrocarbon/olefin mole ratio of from about 1/1 to about 20/1. The resulting products from the reaction are long chain alkyl aromatics, which when subsequently sulfonated have particular application as synthetic detergents;

H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres (about 101 kPa to about 3 MPa), and an aromatic hydrocarbon weight hourly space velocity (WHSV) of from about 1 hr$^{-1}$ to about 50 hr$^{-1}$;

I) The hydrocracking of heavy petroleum feedstocks, cyclic stocks, and other hydrocrack charge stocks. The catalyst will contain an effective amount of at least one hydrogenation component;

J) The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 250° C., a pressure of from about 100 psig to about 800 psig, a WHSV-olefin from about 0.4 hr$^{-1}$ to about 0.8 hr$^{-1}$, a WHSV-reformate of from about 1 hr$^{-1}$ to about 2 hr$^{-1}$ and, optionally, a gas recycle from about 1.5 to about 2.5 vol/vol fuel gas feed;

K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 100° C. to about 400° C. and pressures from about 50 psig to about 450 psig;

L) The alkylation of phenols with olefins or equivalent alcohols to provide long chain alkyl phenols. Typical reaction conditions include temperatures from about 100° C. to about 250° C., pressures from about 1 to about 300 psig and total WHSV of from about 2 hr$^{-1}$ to about 10 hr$^-$;

M) The conversion of light paraffins to olefins and/or aromatics. Typical reaction conditions include temperatures from about 425° C. to about 760° C. and pressures from about 10 psig to about 2000 psig;

N) The conversion of light olefins to gasoline, distillate and lube range hydrocarbons. Typical reaction conditions include temperatures of from about 175° C. to about 375° C., and a pressure of from about 100 psig to about 2000 psig;

O) Two-stage hydrocracking for upgrading hydrocarbon streams having initial boiling points above about 200° C. to premium distillate and gasoline boiling range products or as feed to further fuels or chemicals processing steps. Either stage of the two-stage system can contain catalyst, which contains molecular sieve that is susceptible to loss of catalytic activity due to contact with water molecules. Typical reaction conditions include temperatures of from about 315° C. to about 455° C., pressures of from about 400 to about 2500 psig, hydrogen circulation of from about 1000 SCF/bbl to about 10,000 SCF/bbl and a liquid hourly space velocity (LHSV) of from about 0.1 hr$^{-1}$ to about 10 hr$^{-1}$;

P) A combination hydrocracking/dewaxing process in the presence of a catalyst that contains molecular sieve that is susceptible to loss of catalytic activity due to contact with water molecules. The catalyst generally further comprises a hydrogenation component. Optionally, included in the catalyst is zeolite molecular sieve such as zeolite Beta. Typical reaction conditions include temperatures from about 350° C. to about 400° C., pressures from about 1400 psig to about 1500 psig, LHSVs from about 0.4 hr$^{-1}$ to about 0.6 hr$^{-1}$ and a hydrogen circulation from about 3000 to about 5000 SCF/bbl;

Q) The reaction of alcohols with olefins to provide mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 2 to about 200 atm, WHSV (gram-olefin per hour gram-zeolite) from about 0.1 hr$^{-1}$ to about 200 hr$^{-1}$ and an alcohol to olefin molar feed ratio from about 0.1/1 to about 5/1;

R) The disproportionation of aromatics, e.g., the disproportionation toluene to make benzene and paraxylene. Typical reaction conditions include a temperature of from about 200° C. to about 760° C., a pressure of from about one atmosphere (101 kPa) to about 60 atmospheres (6.1 MPa), and a WHSV of from about 0.1 hr$^{-1}$ to about 30 hr$^{-1}$;

S) The conversion of naphtha (e.g., $C_6$-$C_{10}$) and similar mixtures to highly aromatic mixtures. Thus, normal and slightly branched chained hydrocarbons, preferably having a boiling range above about 40° C., and less than about 200° C., can be converted to products having a substantially higher octane aromatics content by contacting the hydrocarbon feed with a molecular sieve catalyst at a temperature of from about 400° C. to about 600° C., preferably from about 480° C. to about 550° C., at pressures of from one atmosphere (101 kPa) to about 40 atmospheres (4.1 MPa), and liquid hourly space velocities (LHSV) of from 0.1 hr$^{-1}$ to 15 hr$^{-1}$;

T) The adsorption of alkyl aromatic compounds for the purpose of separating various isomers of the compounds;

U) The conversion of oxygenates, e.g., alcohols, such as methanol, or ethers, such as dimethylether, or mixtures thereof to hydrocarbons including olefins and aromatics with reaction conditions including temperatures of from about 275° C. to about 600° C., pressures of from about 0.5 atmosphere (51 kPa) to about 50 atmospheres (5.1 MPa), and a liquid hourly space velocity of from about 0.1 hr$^{-1}$ to about 100 hr$^{-1}$;

V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a molecular sieve catalyst at a temperature in the range of from about 250° C. to about 800° C., a LHSV of from about 0.2 hr$^{-1}$ to about 50 hr$^{-1}$, and a hydrocarbon partial pressure of from about 0.1 to about 50 atmospheres (about 10 kPa to about 5.1 MPa). Temperatures below about 250° C. may be used to oligomerize the feedstock when the feedstock is in the liquid phase when contacting the coated zeolite catalyst. Thus, when the olefin feedstock contacts the catalyst in the liquid phase, temperatures of from about 10° C. to about 250° C. may be used;

W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

In general, reactor conditions include a temperature of from about 100° C. to about 760° C., a pressure of from about 0.1 atmosphere (10 kPa) to about 200 atmospheres (20.3 MPa), a weight hourly space velocity of from about 0.08 hr$^{-1}$ to about 2,000 hr$^{-1}$.

The separation techniques of this invention are particularly suited to large, commercial scale reaction systems. For example, the separation techniques of this invention are particularly suited to reaction systems that require a catalyst loading of at least about 1,000 kg of catalyst, based on total amount of catalyst located throughout the reaction system. In particular, the separation processes of this invention are particularly suited to reaction systems that require a catalyst loading of at least about 10,000 kg of catalyst, more particularly a catalyst loading of at least about 100,000 kg of catalyst, and most particularly a catalyst loading of at least about 250,000 kg of catalyst, based on total amount of catalyst located throughout the reaction system.

Description of Solid Particles

In an embodiment, the apparatus and method of the invention are generally useful for separating any solid particles in a gas-solids flow. In another embodiment, the solid particles can be catalyst particles, such as molecular sieve catalyst particles.

In an embodiment, a molecular sieve catalyst can be characterized according to an Attrition Rate Index (ARI). The ARI methodology is similar to the conventional Davison Index method. The smaller the ARI, the more resistant to attrition; hence, the harder the catalyst. The ARI is measured by adding 6.0±0.1 g of catalyst, having a particle size ranging from 53 to 125 microns, into a hardened steel attrition cup. Approximately 23,700 scc/min of nitrogen gas is bubbled through a water-containing bubbler to humidify the nitrogen. The wet nitrogen is passed through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent catalyst that has broken apart through attrition.

The nitrogen flow passing through the attrition cup is maintained for 1 hour. Fines collected in the thimble are removed from the unit, and a new thimble is installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in wt %/hr.

$$ARI=[C/(B+C)/D]\times 100\%$$

wherein
a. B=weight of catalyst left in the cup after the attrition test;
b. C=weight of collected fine catalyst particles after the first hour of attrition treatment; and
c. D=duration of treatment in hours after the first hour attrition treatment.

In an embodiment, the molecular sieve catalyst of this invention has an ARI of not greater than about 0.6 wt %/hr. Preferably, the molecular sieve catalyst has an ARI of not greater than about 0.5 wt %/hr, more preferably not greater than about 0.4 wt %/hr.

Molecular sieve catalyst particles for use in a gas-solids reaction can be synthesized by a variety of methods. In an embodiment, catalyst particles are synthesized by combining a first dried molecular sieve catalyst with water to make a water-catalyst composition, making a slurry from the water-catalyst composition, and drying the slurry to produce a second dried molecular sieve catalyst. The method particularly provides for the re-manufacturing, recycling or re-working of dried or substantially dried, or partially dried molecular sieve catalysts to yield catalyst particles with properties that are acceptable to the user or manufacturer. Such properties are usually observed after the dried molecular sieve catalyst is calcined. These properties include acceptable particle size, particle size distribution, particle density, and particle hardness.

The catalysts of this invention can include any of a variety of molecular sieve components. The components include zeolites or non-zeolites, preferably non-zeolites. In one embodiment, the molecular sieves are small pore non-zeolite molecular sieves having an average pore size of less than about 5 angstroms, preferably an average pore size ranging from about 3 to 5 angstroms, more preferably from 3.5 to 4.2 angstroms. These pore sizes are typical of molecular sieves having 8 membered rings.

Conventional crystalline aluminosilicate zeolites having catalytic activity are desirable molecular sieves that can be used in making the catalyst of this invention. Non-limiting examples of zeolites which can be employed in the practice of this invention, include both natural and synthetic zeolites. These zeolites include zeolites of the structural types included in the *Atlas of Zeolite Framework Types*, edited by Ch. Baerlocher, W. M. Meier, D. H. Olson, Fifth Revised edition, Elsevier, Amsterdam, 2001.

Zeolites typically have silica-to-alumina ($SiO_2/Al_2O_3$) mole ratios of at least about 2, and have uniform pore diameters from about 3 to 15 Angstroms. They also generally contain alkali metal cations, such as sodium and/or potassium and/or alkaline earth metal cations, such as magnesium and/or calcium. In order to increase the catalytic activity of the zeolite, it may be desirable to decrease the alkali metal content of the crystalline zeolite to less than about 5 wt. %, preferably less than about 1 wt. %, and more preferably less than about 0.5 wt. %. The alkali metal content reduction, as is known in the art, may be conducted by exchange with one or more cations selected from the Groups IIB through VIII of the Periodic Table of Elements (the Periodic Table of Elements referred to herein is given in *Handbook of Chemistry and Physics*, published by the Chemical Rubber Publishing Company, Cleveland, Ohio, 45th Edition, 1964 or 73rd Edition, 1992), as well as with hydronium ions or basic adducts of hydronium ions, e.g., $NH_4^+$, capable of conversion to a hydrogen cation upon calcination. Desired cations include rare earth cations, calcium, magnesium, hydrogen and mixtures thereof.

In another embodiment, the catalyst particles which are flowed through the gas-solids reactor system of this invention are molecular sieve catalysts, such as a conventional molecular sieve. Examples include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW, and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM, and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice*, Second Completely Revised and Expanded Edition, Volume 137, pp. 1-67, Elsevier Science, B. V., Amsterdam, Netherlands (2001).

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. Pat. No. 6,743,747 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992).

The more preferred silicon, aluminum and/or phosphorous containing molecular sieves, and aluminum, phosphorous, and, optionally, silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis: $mR:(M_xAl_yP_z)O_2$ wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO molecular sieves useful herein include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56 and metal containing molecular sieves thereof. Of these, particularly useful molecular sieves are SAPO-18, SAPO-34, SAPO-35, SAPO-44, SAPO-56 and metal containing derivatives thereof. SAPO-34 is particularly preferred.

In another embodiment of the invention, the catalyst used in this invention incorporates aluminophosphate (AlPO) molecular sieves. These molecular sieves can be included as separate crystals or they can be intermixed with other crystalline structures such as by an intergrowth structure. Examples of aluminophosphates include AlPO-5, AlPO-11, AlPO-18, AlPO-31, AlPO-34, AlPO-36, AlPO-37, and AlPO-46.

In one embodiment, the catalyst includes a combination of at least one SAPO and at least one AlPO molecular sieve, wherein the SAPO is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, and SAPO-56, and the AlPO is selected from the group consisting of AlPO-5, AlPO-11, AlPO-18, AlPO-31, AlPO-34, AlPO-36, AlPO-37, and AlPO-46. The sieves can be combined as separate crystals or as intergrown crystals. Preferably, the SAPO is SAPO-18 or SAPO-34, and preferably, the AlPO is AlPO-34 or AlPO-18.

Note that SAPO-18, AlPO-18 and RUW-18 have an AEI framework-type, and SAPO-34 has a CHA framework-type, and that preferred molecular sieves used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are desired. Particularly desired are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691; the catalyst and process descriptions of each being expressly incorporated herein by reference. In general, these methods involve contacting the olefin product with a polyolefin-forming catalyst at a pressure and temperature effective to form the polyolefin product.

Exemplary Embodiments

The techniques of this invention were further implemented and tested in a cold flow test apparatus at near atmospheric pressure and ambient temperature using MTO fluidized catalyst. In the test apparatus, five 20 cm risers were joined together in a system having a single separation vessel with a roughly 1 meter diameter. Air was used as the sparging and transport gas. Flows exiting the risers entered the separation vessel via a cyclone separator. The higher density flows exiting diplegs of a cyclone separator passed down into a transition zone containing 6 levels of baffles or sheds. The 6 levels of baffles or sheds were organized into 3 pairs of levels, with the sheds in each pair rotated by 90 degrees relative to the sheds in an adjacent pair of levels. Within a pair, the sheds were positioned so that an opening in one level of the pair corresponded to a shed location in the other level of the pair.

Figure 6:
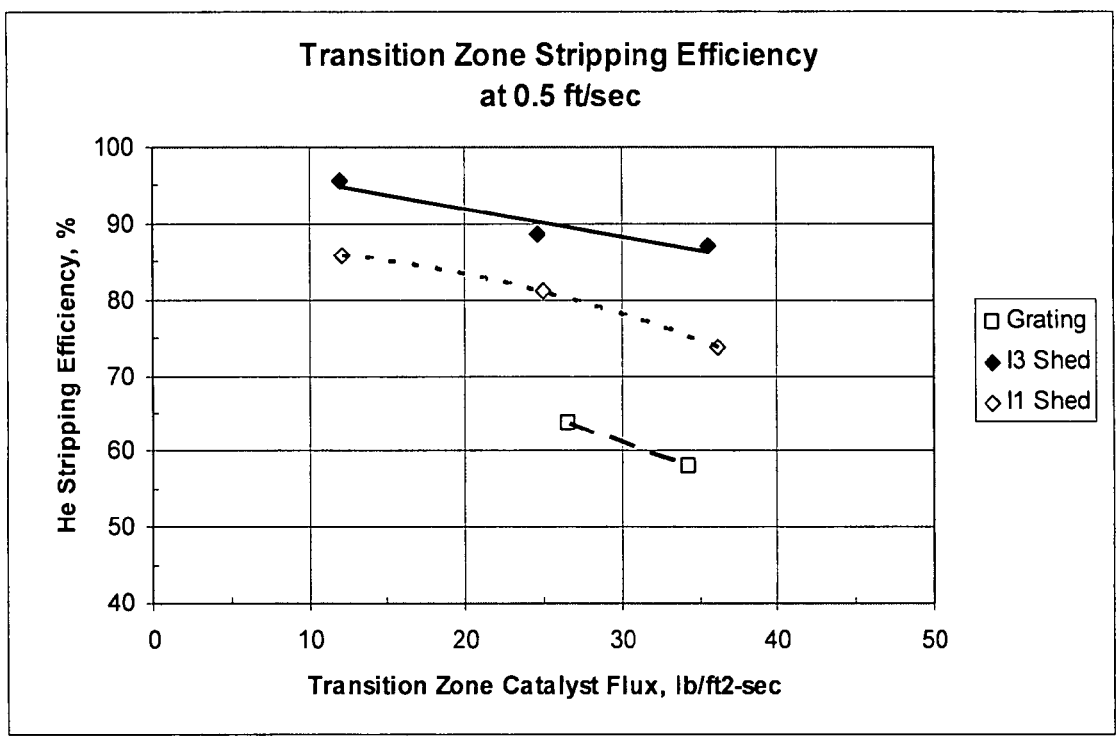
FIG. 6 shows results of operation of an apparatus according to an embodiment of the invention.

To test the ability of the gas spargers and baffles for removing entrained gases, helium was injected into the gas-solids flow as the flow exited the diplegs of the cyclone separators. The removal efficiency was determined by measuring the amount of helium remaining in the solids flow as the solids flow entered the standpipe entry location, as compared to the amount of helium in the solids flow at the top of the bed. FIG. 6 shows the impact of various types of baffles or sheds on the removal efficiency of the helium from the gas-solids flow. The types of baffles used are noted in the figure. The grating baffles are similar to a subway grating consisting of multiple narrow metal slats or strips placed perpendicular to the flow and spaced about every inch with one inch openings between each strip. The I1 sheds represent inverted v-shaped structures. The I3 sheds are similar to the I1 sheds, but additionally have a vertical surface at each of the lower edges of the v-shaped structure and are perforated with holes to allow gas to pass through the shed. Multiple rows of baffles were used in all of the cases shown in FIG. 6. The superficial velocity of air injected by the gas spargers in all cases shown is 0.5 ft/sec (0.15 m/sec).

In FIG. 6, the stripping efficiency of the combination of baffles and stripping gas from the gas spargers is shown relative to the flux of catalyst passing through the transition zone. Stripping efficiency is defined as the percentage of the vapor component entering the top of the transition zone that is displaced and does not enter the standpipe at the bottom of the transition zone. While all of the baffles show some effectiveness in separating helium from the solids, the I3 sheds have the highest percentage removal of the injected helium from the solids flow. The removal efficiency declines as the flux within the transition zone increases (which corresponds to an increase in the flux in the standpipes as well).

Figure 7:
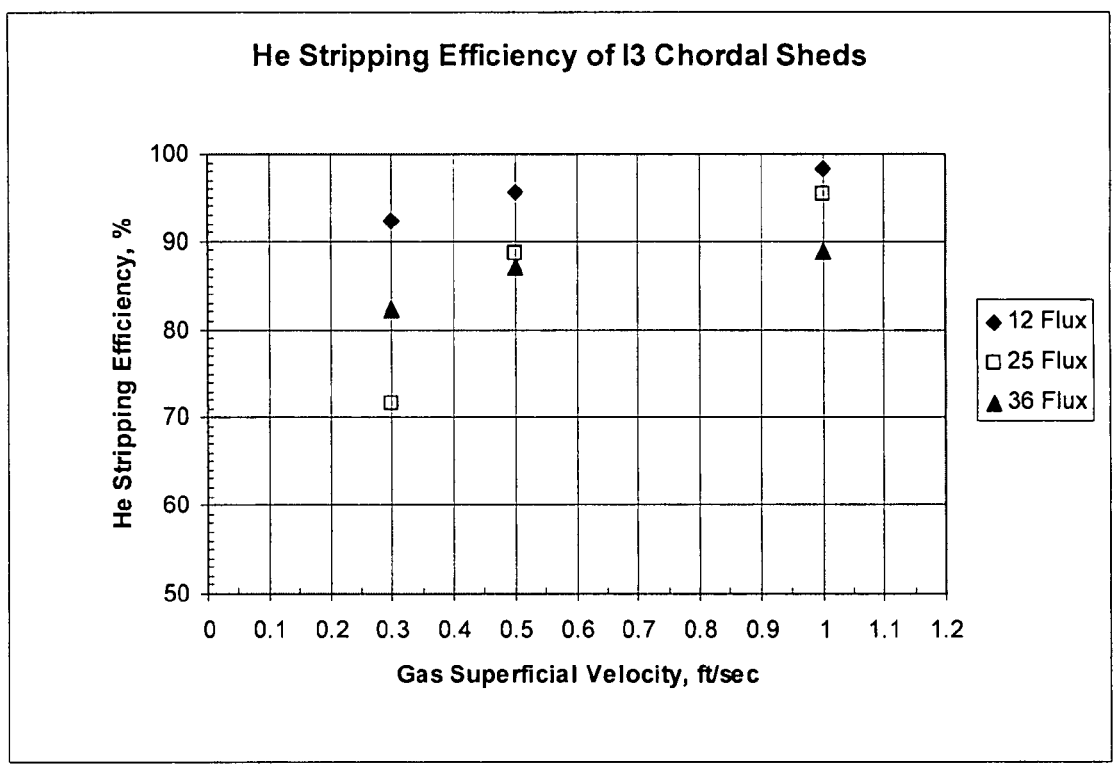
FIG. 7 shows results of operation of an apparatus according to an embodiment of the invention.

FIG. 7 shows the effect of varying the superficial velocity of the sparging gas on the removal efficiency of the helium from the solids flow. The superficial velocity of the sparging gas corresponds to the total flow rate of the gas divided by the cross sectional area of the separation vessel. In these measurements, the I3 style sheds were used. As shown in FIG. 7, the removal efficiency approaches 90% for all transition zone solid flux values when the sparging gas superficial velocity is 0.5 ft/sec (0.15 m/sec) or larger.

In various embodiments, the stripping or displacing efficiency of the stripping gas can be at least 50%, or at least 70%, or at least 90%. Alternatively, the stripping efficiency can be 99.9% or less, or 95% or less.

Figure 8:
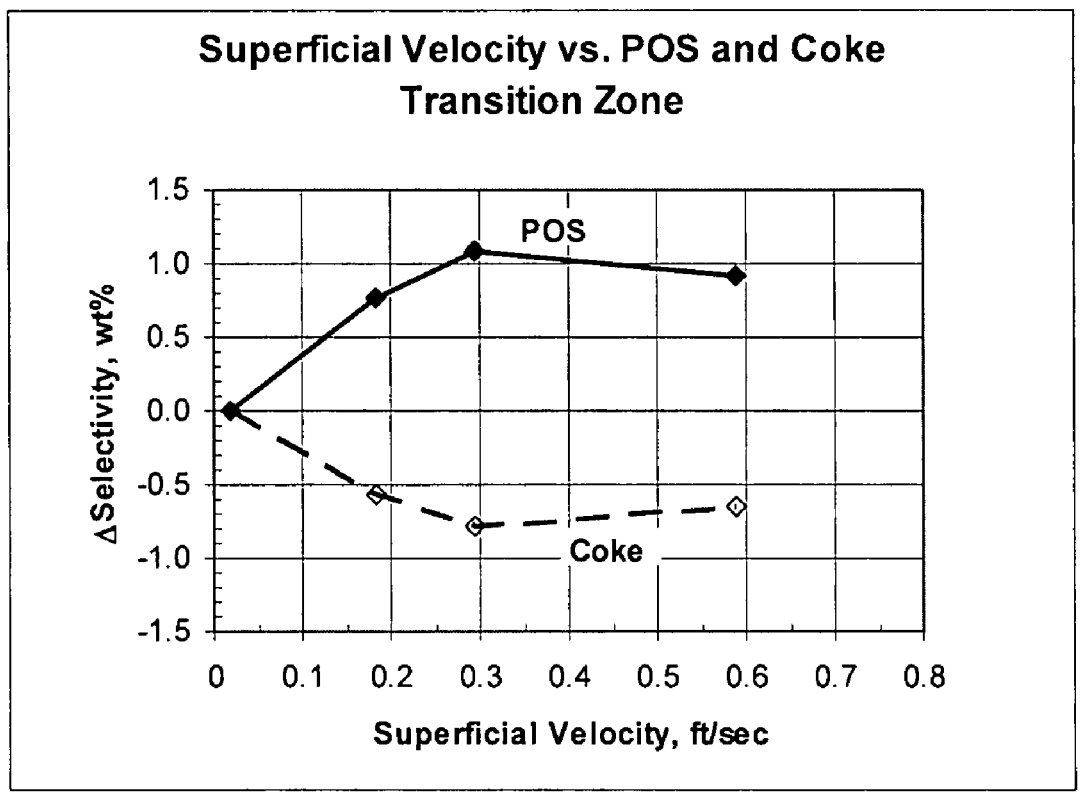
FIG. 8 shows results of operation of an apparatus according to an embodiment of the invention.

FIG. 8 shows the effect of incorporating an embodiment of the invention into a pilot plant for performing a methanol-to-olefin conversion reaction. In FIG. 8, gas spargers were incorporated into the separation vessel for the pilot plant, but no additional baffles were used. FIG. 8 shows the impact on prime olefin selectivity (POS) and coke selectivity from that in a baseline pilot experiment. Selectivity is defined as the weight of the product component divided by the weight of the total product excluding water on a percentage basis. In the baseline experiment, only a minimal flow of sparging gas was flowed through the gas inlets to prevent clogging of the gas inlets by catalyst particles. Increasing the superficial velocity of the sparging gas to 0.2 or 0.3 ft/sec (0.06 or 0.09 m/sec) provided a noticeable increase in the POS while also suppressing coke selectivity. Superficial velocities above 0.3 ft/sec (0.09 m/sec), however, did not appear to provide further improvement in the POS and did not further suppress coke selectivity.

In various embodiments, flowing a stripping gas through the transition zone can produce an increase in POS of at least 0.1%, or at least 0.5%, or at least 1.0%. Alternatively, flowing a stripping gas through the transition zone can produce an increase in POS of 5% or less, or 2% or less. In other embodiments, flowing a stripping gas through the transition zone can produce a decrease in coke selectivity of at least 0.1%, or at least 0.5%, or at least 1.0%. Alternatively, flowing a stripping gas through the transition zone can produce a decrease in coke selectivity of 5% or less, or 2% or less.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

What is claimed is:

1. A method for separating solids from a gas-solids flow comprising:
    producing a plurality of product gas-solids flows by performing an oxygenate to olefin conversion reaction in a plurality of reactors;
    separating each of the plurality of product gas-solids flows into a corresponding higher density flow and lower density flow, each higher density flow comprising a majority of the solids contained in the corresponding product gas-solids flow;
    receiving the solids from each higher density flow in a transition zone;
    flowing a displacing gas, from one or more displacing gas inlets within the transition zone, countercurrently through the received solids while passing the received solids through the transition zone; and
    returning the received solids to the plurality of reactors via standpipes, the entry locations for each standpipe being separated from the one or more displacing gas inlets by a separation distance of at least 25 cm.

2. The method of claim 1, wherein the transition zone comprises a plurality of baffle layers.

3. The method of claim 2, wherein the one or more displacing gas inlets comprise a lowest layer of baffles in the baffled transition zone.

4. The method of claim 1, wherein the transition zone comprises at least one pair of baffle layers.

5. The method of claim 4, wherein an orientation of one layer of the pair of baffle layers is rotated by 90 degrees relative to the second layer of the pair of baffle layers.

6. The method of claim 1, wherein a superficial velocity of the displacing gas within the transition zone is 0.03 m/sec or greater.

7. The method of claim 1, wherein a superficial velocity of the displacing gas within the transition zone is 0.15 m/sec or greater.

8. The method of claim 1, wherein flowing the displacing gas leads to increased reactor effluent prime olefin selectivity and reduced coke selectivity.

9. The method of claim 1, wherein the stripping efficiency within the transition zone is at least 50%.

10. The method of claim 1, wherein the displacing gas is steam.

11. The method of claim 1, wherein the separation distance is at least 50 cm.

12. The method of claim 1, wherein the separation distance is at least 90 cm.

13. The method of claim 1, wherein returning the received solids to the plurality of reactors comprises returning the received solids to at least 4 reactors.

14. The method of claim 1, wherein receiving the solids from each higher density flow further comprises receiving regenerated solids returned from a regenerator.

15. The method of claim 1, wherein a catalyst flux in each standpipe is at least 488 kg/m$^2$*sec.

16. The method of claim 1, wherein a catalyst flux exists in each standpipe, wherein the flux in each standpipe is at least 976 kg/m$^2$*sec.

17. The method of claim 1, wherein a catalyst flux exists in each standpipe, wherein the flux in the transition zone is 488 kg/m$^2$*sec or less.

18. The method of claim 1, wherein a catalyst flux exists in each standpipe, the flux being 122 kg/m$^2$*sec or less.

19. The method of claim 1, wherein a catalyst flux exists in each standpipe, the flux being at least 5 kg/m$^2$*sec.

20. The method of claim 1, wherein a catalyst flux exists in each standpipe, the flux being at least 49 kg/m$^2$*sec.

21. The method of claim 1, wherein a ratio of a distance from a center of the transition zone to a center of a standpipe versus a diameter of the transition zone is at least 0.2.

22. The method of claim 1, wherein a ratio of a distance from a center of the transition zone to a center of a standpipe versus a diameter of the transition zone is at least 0.3.

23. The method of claim 1, possessing a catalyst residence time within the transition zone of 10 minutes or less.

24. The method of claim 1, possessing a catalyst residence time within the transition zone of 1 minute or less.

25. The method of claim 1, possessing a catalyst residence time within the transition zone of 5 seconds or less.

26. The method of claim 1, possessing a catalyst residence time within the transition zone of 30 seconds or less.

27. The method of claim 1, wherein the catalyst density gradient within the transition zone is 525 kg/m$^3$-m or less.

28. The method of claim 1, wherein the catalyst density gradient within the transition zone is 53 kg/m$^3$-m or less.

29. The method of claim 1, wherein a volume fraction of vapor bubbles at the standpipe entry locations is at least 0.00005.

30. The method of claim 1, wherein a volume fraction of vapor bubbles at the standpipe entry locations is at least 0.0002.

* * * * *